US006235491B1

(12) United States Patent
Connolly

(10) Patent No.: US 6,235,491 B1
(45) Date of Patent: May 22, 2001

(54) ASSAY UTILIZING MAGNETIC PARTICLES

(75) Inventor: Patricia Connolly, Glasgow (GB)

(73) Assignee: Byk Gulden Italia S.p.A., Cormano (IT)

( * ) Notice: Subject to any disclaimer, the term of this patent is extended or adjusted under 35 U.S.C. 154(b) by 0 days.

(21) Appl. No.: 09/403,012

(22) PCT Filed: Apr. 20, 1998

(86) PCT No.: PCT/EP98/02308

§ 371 Date: Nov. 19, 1999

§ 102(e) Date: Nov. 19, 1999

(87) PCT Pub. No.: WO98/48282

PCT Pub. Date: Oct. 29, 1998

(30) Foreign Application Priority Data

Apr. 18, 1997 (EP) .................................................. 97302671

(51) Int. Cl.[7] .............................. C12Q 1/58; C12Q 1/54; C12Q 1/26

(52) U.S. Cl. .................................. 435/12; 435/14; 435/25; 435/4; 435/7.91; 435/7.1; 435/287.1; 205/787.5; 204/175

(58) Field of Search ................................ 435/12, 14, 975, 435/25, 7.91, 4, 7.1; 205/787.5; 204/175

(56) References Cited

FOREIGN PATENT DOCUMENTS

| 872736 A1 | * 10/1998 | (EP) . |
| 2 284 890 | 6/1995 | (GB) . |
| 89/10788 | 11/1989 | (WO) . |
| 94/19690 | 9/1994 | (WO) . |
| 94/28414 | 12/1994 | (WO) . |
| 95/06868 | 3/1995 | (WO) . |

* cited by examiner

Primary Examiner—Louise N. Leary
(74) Attorney, Agent, or Firm—Jacobson, Price, Holman & Stern, PLLC

(57) ABSTRACT

An assay for the presence of an analyte or determining a biological or medical parameter comprising the steps of adding an assay component to a pH-sensitive material charged with magnetic particles, wherein the assay component causes a pH change which is a function of the analyte or parameter to be measured; subjecting the magnetic particles to an oscillating magnetic field; and measuring the effect of the magnetic field on the magnetic particles. The assay is an enzyme immunoassay. A kit for practicing the enzyme immunoassay is also described.

15 Claims, 2 Drawing Sheets pH polymer
and magnetic
particle mix
replaces current
magnetic particle
chamber

ASSAY UTILIZING MAGNETIC PARTICLES

The present invention relates to assay for the pressure of an analyte or for determining a biological or medical parameter and to a kit for such an assay.

When a patient is treated by a physician, it is not uncommon for the physician to take samples of body fluids to be sent on to a laboratory for analysis. Such testing inevitably gives rise to some delay in the processing of the sample. This is particularly true where samples have to be sent to a separate laboratory for testing. Even in hospitals it can often take a number of hours for the results to be communicated back to the physician. Accordingly, it is not uncommon for the physician to begin treating a patient without knowing the results of any requested testing.

It situations where the patient is seriously ill, the delay incurred in testing samples could conceivably put the well-being of that patient at risk.

One might consider that a suitable way to overcome this problem would be for the physician in charge of a particular patient to conduct the testing himself, without sending the samples away to a laboratory. However, the testing of samples is often a complex process which must be carried out by highly trained personnel if the results are to be reliable and hence of any real use to the physician.

Therefore, there is a need in the art for assays which can be quickly and reliably carried out by a user (who will sometimes be referred to as in operator), particularly for samples obtained from patients.

GB-A-2,284,890 relates to an analyte sensor in which an analyte is detected by reacting it with an enzyme or catalytic species at or very near to a polymer coated electrode. The enzyme or catalytic species directly or indirectly effects a reaction with said polymer layer wherein the polymer layer becomes porous causing a measurably change in electrical properties at the electrode surface. In one embodiment the polymer is pH-sensitive and the reactions cause a change in pH.

WO98/10788 relates a method for the measurement of clot formation times, clot dissolution time or clotting parameters by monitoring movement of magnetic particles in the sample being assayed, where the movement is induced by a magnetic field.

WO94/19690 relates to a method for performing an affinity assay and which monitors the response of an oscillating field on magnetic particles to determine the analyte concentration.

WO95/06868 also describes an oscillating particle type coagulation assay.

The present invention provides a method of testing samples, especially patient samples. Advantages of this method include the fact that the assay can use whole blood, hence avoiding a pre-assay step involving separation of blood components. The method of the present invention can be automated and will make the results of the test available quickly and thus provide an early and rapid diagnosis of a patient's condition. The method is simply and therefore minimal operator skill is required. In addition, the equipment necessary to automate the method may be readily available and therefore the method will be economic.

In its broadest aspect the present invention provides a method for carrying out an assay which has as its end point a pH change.

In a first aspect, the present invention provides an assay for the presence of an analyte or determining a biological or medical parameter comprising the following steps:
an assay component is added to a pH-sensitive material charged with magnetic particles, wherein the assay component causes a pH change which is a function of the parameter to be measured;
subjecting the magnetic particles to an oscillating magnetic field; and measuring the effect of the magnetic field on the magnetic particles.

The presence of the analyte is determined, or determination of the parameter is made, using analysis of the response of the magnetic particles to the magnetic field.

It will be appreciated that the pH material is changed as a function of the analyte or parameter and this results in a change in the movement of the magnetic particles in the oscillating magnetic field.

The sample may be aqueous, whole blood, serum, plasma, urine or saliva.

In a second aspect, there is provided a method for carrying out an assay for the presence of an analyte, comprising:
contacting a sample to be assayed for the presence of an analyte with a reactive species, the analyte reacting with the reactive species resulting in a change in pH;
directly or indirectly effecting a reaction with a pH-sensitive material, which is charged with pH-sensitive material magnetic particles;
applying a magnetic field to the magnetic particles;
monitoring a response of said magnetic particles to the magnetic field; and
determining the amount of analyte in said sample by analysis of the response of the magnetic particles.

The change in pH is a function of the presence of the analyte.

The interaction of the analyte with the reactive species gives rise to an assay component and the assay component results in the change in pH.

The analyte and reactive species interact to form an assay component such that the pH change is a function of the presence of the analyte. This function may be allow a qualitative or quantitative determination of the amount of analyte present in the sample.

Preferably the assay employs binding pairs. A non-exclusive list of commonly used binding pairs includes avidin/biotin, antibody/antigen, haptens and nucleic acid (DNA and RNA). Generally when the binding pair is antibody/antigen the assay is referred to as an immunoassay. Other biosubstances capable of molecular recognition include lectins for saccharides, hormone receptors for hormones and drug receptors for drugs and active drug metabolites.

In a preferred aspect the method is used for performing an immunoassay.

In a third aspect, the present invention relates to an enzyme immunoassay in which the pH produced by the enzyme reaction is a function of the amount of analyte, and wherein liberation of magnetic particles from a pH-sensitive material is detected.

As changes in pH are associated with many enzyme reactions the present invention provides a flexible assay with wide applicability. Generally, in enzyme immunoassays, the enzyme is used as a label or marker which is bound to one member of the antigen-antibody pair identical to that in the sample to be measured. The enzyme bound antigen/antibody then competes with the sample antigen/antibody for the binding site on a limited supply of its complement antibody/antigen.

Classical methods for immunoassay include:
(i) A capture antibody on a solid phase, such as a plastic microtitre plate, exposure to the biological sample to attach the antigen of interest, washing and then exposure to a second labelled antibody. The label on the antibody may be an enzyme for example. Further washing is followed by detection of the label (and hence the amount of antigen in the original sample). This is known as a sandwich assay or two-site assay, or (ii) A capture antibody on the solid phase followed by exposure to the biological sample containing antigen and an added amount of labelled antigen. Labelled and unlabelled antigen compete on the solid phase for the antibody sites. The amount of label revealed after washing is inversely proportional to the amount of true antigen in the biological sample. This is known as a competitive assay.

Other immunoassays methods which are known, or become known, to a skilled worker may also be used. For example, the assay may use direct molecular recognition. In this approach, one of the binding pair, e.g. an antibody, which is immobilised binds with its binding pair present in the sample, causing a pH change. The advantage of direct-recognition assays is simplicity.

In enzyme immunoassays the label is measured by adding the enzyme substrate and monitoring the product by a suitable method. In the present case, the enzyme reaction gives rise to a pH change and this monitored using the effect of a magnetic field on magnetic particles captured in a pH-sensitive material. The signal is then processed and a result calculated.

In another preferred aspect the method of the present invention is used for performing an assay for biological or medical parameters.

Thus, according to a fourth aspect of the present invention there is provided a method for carrying out an assay for biological and medical parameters, comprising:
contacting a sample to be assayed for a biological or medical parameter with a reactive species causing an assay component to be developed which is a function of the parameter to be measured and resulting in a change in pH;
directly or indirectly effecting a reaction with a pH-sensitive material which is charged with magnetic particles;
applying a magnetic field to the magnetic particles;
monitoring a response of said magnetic particles to the magnetic field; and
determining the parameter by analysis of the response of the magnetic particles.

The change in pH is a function of the biological or medical parameter.

The interaction of the sample with the reactive species gives rise to an assay component and the assay component results in the change in pH.

The sample and reactive species interact to form an assay component, which results in a pH change which is a function of the parameter to be determined. This function may be allow a qualitative or quantitative determination of the parameter of interest.

The biological or medical parameters may include clinical chemistry parameters, typically blood electrolytes and metabolites, or blood gas measurement.

In a preferred embodiment, particularly for clinical chemistry or blood gas assays, the sample is exposed to a combination of reagents, normally enzymes and substrates, which cause an assay component to be developed in proportion to the presence of the analyte of interest. Thus, according to another aspect of the present invention there is provided an assay for biological or medical parameters, such as clinical chemistry or blood gas measurements, in which a sample containing an analyte mixes with reagents suitable to cause a pH change in proportion to the analyte concentration. It will be appreciated that in this case the analyte corresponds to the parameter of interest.

The method of the present invention is described below mainly in connection with immunoassays; however, it will be appreciated that the general description is equally applicable to other assays such as the measurement of biological or medical parameters.

The amount or presence of analyte may be determined by analysis of the time varying signal of the magnetic particles as they are subjected to the oscillating magnetic field.

The magnetic field may be generated by the use of a static or moving magnetic field. Preferably the oscillating field is generated by an oscillating field generating device which is itself stationary.

In a preferred embodiment the assay uses a small chamber containing the magnetic particles captured in the pH-sensitive material. The assay component is added to the chamber. The magnetic particles are subject to an oscillating magnetic field. This movement is detected by monitoring the light reflected from a source shown down onto the chamber. As the particles stand up reflected light from the card is reflected onto a photodetector placed above the chamber. As the particles lie down the light is blocked and a minimum is reached on the photodetector. As the pH-sensitive material dissolves or disintegrates the particles become freed to move and the level of light reflected changes, preferably in a specific time dependent way.

Preferably the chamber forms part of a plastic card system.

The polymer is preferably in the form of a thin film and is generally almost translucent. Enteric polymers can be selected which have the property of dissolving at a specific pH in solution.

An assay can be designed in wicking format which creates a pH change in a suitable buffer solution or in the patient sample itself. The pH changes will be dependent upon the quantity of analyte present, and this causes the polymer to dissolve and the particles to move. The movement of the particles would be detected as a change in reflected light levels. The time dependent behaviour of the reflected light would be used to calibrate the immunoassay.

Conveniently the magnetic particles are fixed in the pH-sensitive material by cross-linking the molecules of the pH-sensitive material thereby trapping or capturing the magnetic particles.

The present invention involves the partial or complete removal of the pH-sensitive material from around the magnetic particles. As previously mentioned, preferably the present invention relates to an enzymatic immunoassay. Generally in this embodiment, the enzyme or catalyst produces a product which can react with the polymer, or can directly hydrolyse the polymer membrane.

The enzymes or catalysts may be bound within or directly to the polymer e.g. bound to the polymer via an antibody-antigen interaction with an enzyme-labelled conjugate, bound to a porous membrane in close proximity to the pH-sensitive material, or be present in the bulk solution. Preferably, the enzymes or catalysts will be contained in a second reaction chamber, the product of the enzyme reaction (also known in the present invention as the assay component) then entering the chamber containing the pH-sensitive material and magnetic particles.

One of the many appropriate combinations of an enzyme with a polymer coating is the combination of urease with materials such as those used in enteric coatings for tablets. These coating work by being insoluble at the low pH of the stomach, but are soluble at the pH in the intestine (pH 6 and above). Examples of such coating materials are cellulose acetate hydrogen phthalate, methyl vinyl ether-maleic anhydride copolymer esters, anionic polymerisates of methacrylic acid and esters of methacrylic acid (Eurragit® of Rohm-Pharma, Darmstadt, Germany).

In one particular reaction, urease catalyses the breakdown of urea to ammonia and carbon dioxide according to the following scheme:

$$H_2O + urea \rightarrow 2NH_3 + CO_2$$

$$NH_3 + H_2O \rightarrow NH_4^+ + OH^-$$

The resulting increase of the pH value leads to a solubilization of the polymer.

If an antibody is immobilized onto said pH-sensitive polymers, it may capture an urease-labelled conjugate in an immunoassay. The bound urease conjugate then produces a local pH change that leads to the solubilisation of the polymer at the point of conjugate capture. We have found that local solubilisation can occur in solutions where, because of the buffering capacity of the bulk solution, a significant pH change in the solution does not take place. Since assays according to this invention do not require a wash step they can fulfil all the requirements of homogenous assays.

In another embodiment, it is possible to use an $H_2O_2$-producing enzyme such as glucose oxidase in conjunction with Fenton's reaction. This reaction is commonly used in synthetic organic chemistry to hydroxylate aromatics, and works by producing the extremely reactive radical OH•; e.g.

$$H_2O_2 + Fe^{2+} \rightarrow Fe^{3+} + OH^- + HO•$$

The hydroxyl radical is so reactive that it survives only until it encounters an organic species. In this case a polymer coating is chosen which contains structural elements reacting with the HO radicals. The introduction of hydroxyl groups enhances the solubility of the coating.

The assay according to the present invention may be carried out in many different formats known to the skilled worker.

So it is possible to immobilise in any manner known to the man skilled in the art, an antibody at the polymer surface, or preferably in a second reaction chamber, for which the analyte to be measured and an analyte enzyme conjugate or an analyte analogue enzyme conjugate compete.

For a sandwich format immunoassay a first antibody against the analyte to be measured is immobilised at the pH-sensitive material and a second antibody labelled with an enzyme is present in the solution. The first antibody binds the antigen (analyte) of interest in the sample. The second antibody, labelled with an enzyme, binds to the captured antigen. A substrate is present which is converted by the enzyme to the assay component causing a pH change.

For a competition format, a capture antibody is immobilised on a solid phase and then a sample is added containing labelled and unlabelled antigen which compete the antibody sites on the solid phase. The amount of label revealed is inversely proportioned to the amount of antigen in the sample.

In one embodiment of a competition format the solution contains a biotin labelled analyte or a biotin labelled analogue of the analyte. An enzyme conjugate with avidin is also present in the solution or may be added after the capture reaction of the biotin labelled analyte or analyte analogue and the analyte to be measured with the immobilised antibody. Other binding pairs instead of avidin/biotin, e.g. IgG:anti-IgG may be used equally.

As previously mentioned, it is also possible to use a competitive assay where an analyte or an analogue of the analyte is conjugated with an anti-enzyme antibody. Also present in solution is the analyte to be measured and free enzyme, where the signal generated is inversely proportional to the analyte concentration being measured.

In a preferred format, the interaction between the analyte and an enzyme conjugate of the analyte or a analogue of the analyte with an enzyme can be performed in a wick (bibulous layer) or a capillary channel in which an antibody against the analyte is immobilized on the surface. After having passed the wick or capillary channel, the unbound enzyme conjugate of the analyte comes into contact with the material where an anti-enzyme antibody is immobilised. The signal generated is proportional to the concentration of analyte present.

In a further preferred embodiment, the reagent systems may be designed to allow clinical chemical parameters, including blood gas measurement, to be carried out on the same instrument.

Various preferred features and embodiments of the present invention will now be described by way of non-limiting example, with reference to the accompanying drawing, in which:

EXAMPLE 1

Figure 1:
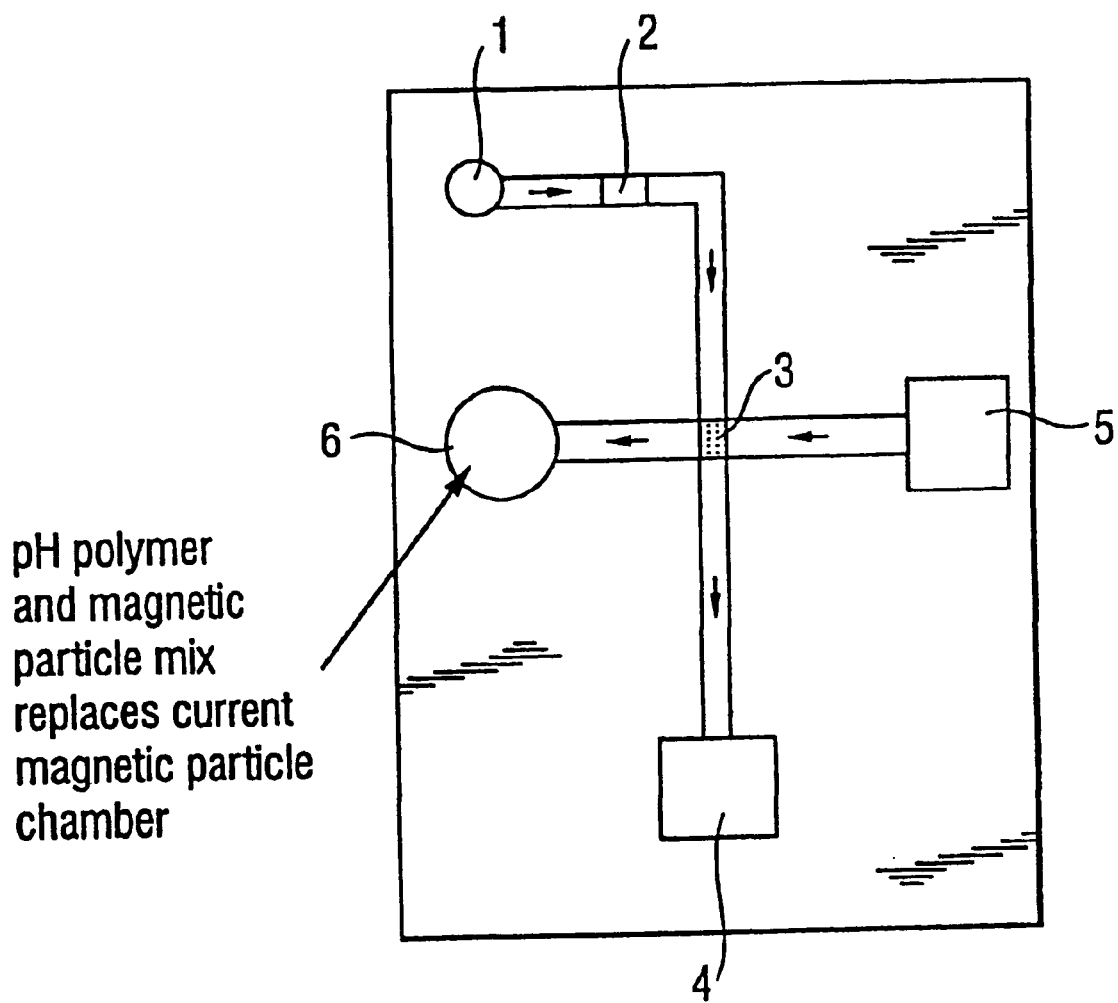
FIG. 1 shows a schematic layout of an assay in accordance with one embodiment of the present invention suitable for detecting an analyte.

This assay is described with reference to FIG. 1.

Steps:

a) Whole blood is added over blood separation membrane 1. The plasma flows along channel to area 2.

b) Antigen picks up tracer antibody at area 2. The tracer antibody is labelled with an enzyme which can cause a pH change when in the presence of its corresponding substrate (e.g. urease).

c) Capture antibody at area 3 binds antigen-labelled antibody conjugate. Excess sample and tracer antibody is drawn off by a wicking action into absorbent area 4.

d) An enzyme substrate (e.g. urea) is released from urea 5 and washes over area 3 causing a pH change when it contacts the enzyme label.

e) A solution with a pH which varies over time arrives at pH-sensitive material and magnetic particle mix in chamber 6.

f) The pH-sensitive material begins to dissolve in a time-dependent manner which is a function of antigen concentration. The magnetic particle are able to move in an applied oscillating magnetic field and cause changes in reflected light which are detected.

The reagent sample flow between areas 4, 5 and 6 may be controlled by any convenient means, such as pressure contact changes to control flow area and open substrate material.

EXAMPLE 2

Figure 2:
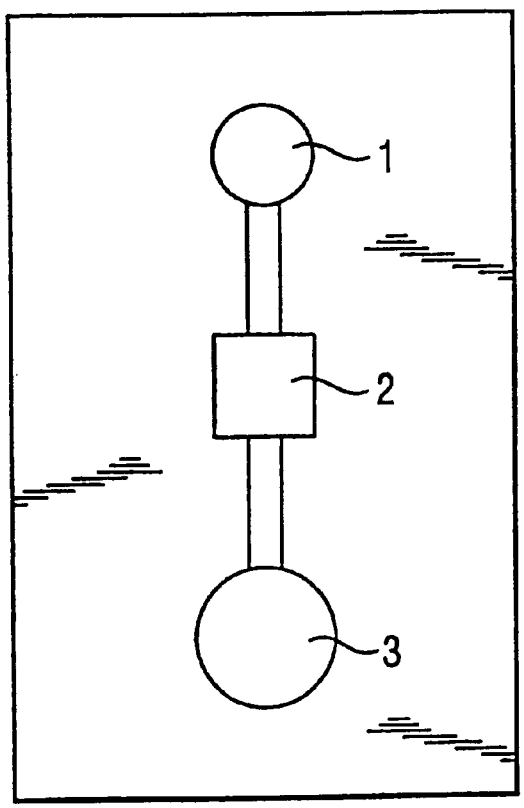
FIG. 2 shows a schematic layout of an assay in accordance with another embodiment of the present invention suitable for the analysis of parameters of biological or medical interest.

This assay is described with reference to FIG. 2.

a) Whole blood is added over sample chamber 1. In one embodiment sample chamber 1 contains a blood separation membrane. In another embodiment, it is simply a chamber for introducing sample to the diagnostic test card.

b) Whole blood or plasma is channelled by wicking, or flows along the card, to reaction area 2. The sample mixes with the reagents in area 2 which are selected to as to cause a pH change related to the parameter to be measured.

c) The reacted liquid flows, or is drawn by wicking, into chamber 3 which contains the pH-sensitive material and magnetic particle mix.

d) The pH-sensitive material begins to dissolve in a time dependent manner which is a function of the concentration of the parameter being measured. The magnetic particles are able to move in an applied oscillating magnetic field and cause changes in reflected light which are detected.

It will be appreciated that the above tests can be carried out on a test card, which is preferably about the size of a credit card, having a reaction chamber containing paramagnetic iron oxide particles captured in the pH-sensitive material.

In order to run a test a sample drop is added to the card in an appropriate well, which could be the chamber itself containing the magnetic particles and pH-sensitive material of a separate reaction chamber. In the present Examples the sample drop would be added to area 1 as shown in FIGS. 1 and 2.

The photodetector detects any change in the light from the added sample. While the test is in progress an electromagnet turns on and off every second. As the paramagnetic particles in the test card became freed they stand up when the magnet is on, causing more light to pass to the photodetector. When the magnetic is off, the particles fall down causing less light to be detected. The movement of these particles produces the signal. Disintegration of the pH-sensitive materials causes the particles to start movement. The analyser monitors particle movement.

Figure 3:
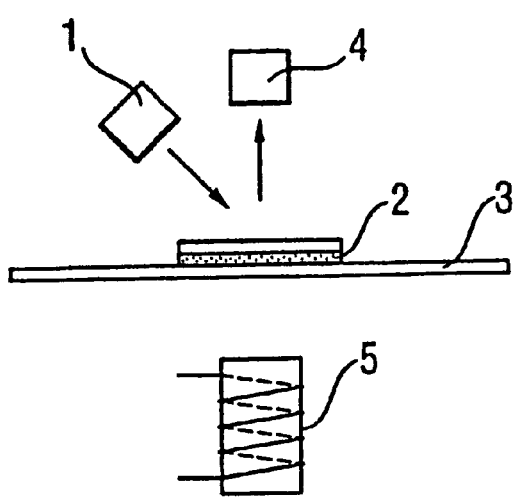
FIG. 3 shows a schematic layout of a method of detection in accordance with one embodiment of the present invention.

As illustrated in FIG. 3, an optical sensor 1 produces light which is directed to a sample 2 on a test card 3. The sample has no or a transparent cover. Light from the source reflects off a reflecting surface beneath the cover. The reflected rays pass into a photodetector 4. An electromagnetic which generates the oscillating magnetic field is shown at 5.

What is claimed is:

1. An assay for the presence of an analyte or determining a biological or medical parameter comprising:
   adding an assay component to a pH-sensitive material charged with magnetic particles, wherein the assay component causes a pH change which is a function of the analyte or parameter to be measured;
   subjecting the magnetic particles to an oscillating magnetic field; and
   measuring the effect of the magnetic field on the magnetic particles.

2. The assay according to claim 1 wherein the assay component results from the interaction of the sample to be assayed with a reactive species.

3. An assay for the presence of an analyte, comprising:
   contacting a sample to be assayed for the presence of an analyte with a reactive species, the analyte interacting with the reactive species resulting in a change in pH;
   directly or indirectly effecting a reaction with a pH-sensitive material which is charged with magnetic particles;
   applying a magnetic field to the magnetic particles;
   monitoring a response of said magnetic particles to the magnetic field; and
   determining the amount of analyte in said sample by analysis of the response of the magnetic particles.

4. An assay for determining a biological or medical parameter, comprising:
   contacting a sample to be assayed for a biological or medical parameter with a reactive species, the sample interacting with the reactive species resulting in a change in pH;
   directly or indirectly effecting a reaction with a pH-sensitive material which is charged with magnetic particles;
   applying a magnetic field to the magnetic particles;
   monitoring a response of said magnetic particles to the magnetic field; and
   determining the parameter by analysis of the response of the magnetic particles.

5. The assay according to claim 2 wherein the reactive species is urease or glucose oxidase.

6. The assay according to claim 1 wherein the assay component is a hydroxyl radical.

7. The assay according to claim 1 wherein the pH-sensitive material is an enteric polymer, acetate hydrogen phthalate, a methyl vinyl ether-maleic anhydride ester, an anionic polymerisate of or an ester of.

8. The assay according to claim 1 wherein the assay is an immunoassay.

9. A kit for performing the assay of any of claims 1–8 comprising a reaction chamber containing magnetic particles captured in an pH-sensitive material, means for generating a magnetic field and detection means.

10. A binding pair assay in which a binding pair reaction produces a pH which is a function of the presence of an analyte in a sample or biological or medical parameter of a sample, and which comprises detecting liberation of magnetic particles from a pH-sensitive material.

11. The assay according to claim 3 wherein the reactive species is urease or glucose oxidase.

12. The assay according to claim 4 wherein the reactive species is urease or glucose oxidase.

13. The assay according to claim 5 wherein the reactive species is urease or glucose oxidase.

14. The assay according to claim 7 wherein the pH-sensitive material is an enteric polymer selected from the group consisting of cellulose acetate hydrogen phthalate, a methyl vinyl ether-maleic anhydride ester, an anionic polymerisate of methacrylic acid and an ester of methacrylic acid.

15. The assay according to claim 1 wherein the assay is an enzyme immunoassay.

* * * * *

UNITED STATES PATENT AND TRADEMARK OFFICE
CERTIFICATE OF CORRECTION

PATENT NO.    : 6,235,491 B1
DATED         : May 22, 2001
INVENTOR(S)   : Patricia Connolly It is certified that error appears in the above-identified patent and that said Letters Patent is hereby corrected as shown below:

Column 1,
Line 38, "WO 98/10788" should read -- WO 89/10788 --

Column 8,
Lines 35-37, "polymer...of or an ester of" should read -- polymer --.

Signed and Sealed this

Sixth Day of August, 2002

Attest:

Attesting Officer

JAMES E. ROGAN
Director of the United States Patent and Trademark Office